United States Patent
Buck

(10) Patent No.: US 10,568,907 B1
(45) Date of Patent: Feb. 25, 2020

(54) METHODS OF TREATING BASAL CELL CARCINOMA AND GLIOBLASTOMA

(71) Applicant: Carol J. Buck, Princeton, NJ (US)

(72) Inventor: Carol J. Buck, Princeton, NJ (US)

( * ) Notice: Subject to any disclaimer, the term of this patent is extended or adjusted under 35 U.S.C. 154(b) by 0 days.

(21) Appl. No.: 16/393,053

(22) Filed: Apr. 24, 2019

Related U.S. Application Data

(63) Continuation-in-part of application No. 16/155,558, filed on Oct. 9, 2018, now Pat. No. 10,369,170.

(51) Int. Cl.

| | | |
|---|---|---|
| *A61K 35/04* | (2006.01) | |
| *A61P 35/00* | (2006.01) | |
| *A61K 9/00* | (2006.01) | |
| *A61K 47/44* | (2017.01) | |
| *A61K 36/87* | (2006.01) | |
| *A61K 45/06* | (2006.01) | |

(52) U.S. Cl.
CPC .............. *A61K 35/04* (2013.01); *A61K 9/007* (2013.01); *A61K 9/0019* (2013.01); *A61K 36/87* (2013.01); *A61K 47/44* (2013.01); *A61P 35/00* (2018.01); *A61K 45/06* (2013.01)

(58) Field of Classification Search
CPC ................ A61K 35/04; A61P 35/00
See application file for complete search history.

(56) References Cited

U.S. PATENT DOCUMENTS

| | | |
|---|---|---|
| 3,987,202 A | 10/1976 | Okun |
| 5,354,475 A | 10/1994 | Bakker |
| 6,337,337 B1 | 1/2002 | Buck |
| 2009/0238754 A1 | 9/2009 | Wegrzyn et al. |

FOREIGN PATENT DOCUMENTS

| | | |
|---|---|---|
| WO | 2009/117042 A1 | 9/2009 |

OTHER PUBLICATIONS

Adamson et al., "Glioblastoma multiforme: a review of where we have been and where we are going," Expert Opin. Investig Drugs Aug. 2009;18(8):1061-83. PMID: 19555299. (Year: 2009).*
Neidle (Ed.), "Cancer Drug Design and Discovery," Academic Press, pp. 427-431 (2008). (Year: 2008).*
Mukherjee. (2010). "The emperor of all maladies: A biography of cancer." New York ; Toronto: Scribner, p. 80 (Year: 2010).*
Roberts, "Coal Tar" in Reference Module in Biomedical Sciences Encyclopedia of Toxicology (3rd Ed.) 2014, pp. 993-995 Encyclopedia of Toxicology. (Year: 2014).*
http://www.cooperscreekchemical.com/pdf/coaltar.pdf, accessed Aug. 2018.
Spectrum Chemical; CAS No. 8007-45-2, https://us.vwr.com/store/product/21572718/spcmc1290, accessed Aug. 2018.

* cited by examiner

*Primary Examiner* — Theodore R. West
(74) *Attorney, Agent, or Firm* — Meagher Emanuel Laks Goldberg & Liao, LLP

(57) ABSTRACT

Provided herein are methods of treating basal cell carcinoma or glioblastoma by administering coal tar or a coal tar product to a patient with basal cell carcinoma or glioblastoma. The coal tar or coal tar product may be administered as a standalone therapy or in combination with other treatments for basal cell carcinoma or glioblastoma.

17 Claims, 9 Drawing Sheets

METHODS OF TREATING BASAL CELL CARCINOMA AND GLIOBLASTOMA

CROSS-REFERENCE TO RELATED APPLICATIONS

This application is a continuation-in-part of U.S. application Ser. No. 16/155,558, filed on Oct. 9, 2018, which is herein incorporated by reference in its entirety.

FIELD OF THE INVENTION

The present application is directed to methods of treating basal cell carcinoma and glioblastoma by the administration of coal tar and/or coal tar products.

BACKGROUND OF THE INVENTION

Basal Cell Carcinoma

The basal layer of mammalian epidermis, or stratum germinativum, is the deepest layer of the five layers of the epidermis and produces new skin cells as existing cells die off. It forms a continuous layer of cells and becomes neoplastic, in most cases, after long-term exposure to ultraviolet light from the sun or artificial sources such as tanning beds that result in damage to the cells' DNA. Basal cell carcinoma (BCC) most commonly appears on skin of the head, neck, and arms and less often on areas of the body covered by clothing such as the trunk and legs. The appearance of BCC varies considerably, presenting as a growth or sore that does not heal or as a translucent, pink, pearly white, brown, black, or blue slightly raised growth. Occasionally, it may be a white, scar-like lesion called morpheaform BCC, with a waxy appearance. In rare cases, BCC can migrate to nearby muscle, nerve, or bone, causing loss or damage to these tissues. A schematic depiction of a BCC is shown in FIG. 1.

Current treatments for BCC include in-office surgical excision, cryosurgery (liquid nitrogen freezing), curettage-electrodessication, electro-surgery (burning with an electric needle), topical chemotherapy, with agents such as 5-fluorouracil (5-FU) and imiquimod, radiation (disks), electronic skin surface brachytherapy (ESSB), and laser therapy. Mohs surgery is used on larger BCC tumors with a high risk of recurrence and involves repeated surgical removal and freezing of cells, layer by layer, following immediate microscopic examination of each layer to determine if there are any remaining cancerous cells, until none are detected. This is followed by closure of the opening with sutures, skin grafts, or plastic surgery, if necessary. Mohs surgery has the highest rate of cure and is used often for BCC on the face where the need to preserve skin is paramount.

Glioblastoma

Glioblastoma is a stage IV glioma, a cancer of the glial cells of the brain and spinal cord. Glioblastomas are aggressive malignancies, always fatal, and the most common type of brain tumor. Once glioblastomas are present, a patient's expected median overall survival is between 14 and 17 months. The glioblastomas form from a type of cell called an astrocyte; they are thus sometimes referred to as astrocytomas. According to Wikipedia, "glioblastomas can contain more than one cell type (i.e., astrocytes, oligodendrocytes). Also, while one cell type may die off in response to a particular treatment, the other cell types may continue to multiply. Glioblastomas are the most invasive type of glial tumors as they grow rapidly and spread to nearby tissue. Approximately 50% of astrocytomas are glioblastomas and are very difficult to treat." Glioblastoma multiforme (GBM) accounts for over 60% of all brain tumors in adults. Hanif et al., 2017, Asian Pac. J. Cancer Prev. 18:3-9. The incidence of glioblastoma is 3.19 per 100,000. Thakkar et al., 2014, Cancer Epidemiol. Biomarkers Prev. 10:1985-96.

Standard therapy consists of surgical resection, followed by radiotherapy within one to four weeks, followed by chemotherapy. Robotic stereotactic radiosurgery is often preferred when the tumor is considered inoperable due to location in the brain or patient health. Experimental treatments include immuno-modulators, biopharmaceuticals, such as antibody drug conjugates, boron neutron capture therapy and gene therapy. One such gene therapy is VAL-083, (dianhydrogalactitol), a DNA-targeting agent currently undergoing Phase 2 and Phase 3 clinical trials. Murphy et al., Transl Res. 2013 April; 161(4): 339-354. Ad-RTS-hIL-12, an inducible adenoviral vector encoding human pro-inflammatory cytokine interleukin-12 (IL-12), plus veledimex, an oral activator ligand, is in clinical development for the treatment of recurrent or progressive glioblastoma multiforme in adults and been shown to extend life expectancy by approximately 6 months beyond current standards of care.

By the time one feels the symptoms of a glioblastoma, its tentacles are widespread in the brain. Injection into the tumor is currently not advisable because the tentacles wrap around the neurons of the brain without a visible center where the nucleus would normally be found in other cancers. Because there is no known method of locating the nucleus, injection into the tumor is usually ineffective. Surgery is generally the first course of treatment resulting in relief of symptoms due to a reduction in pressure caused by the bulk of the tumor within the cranial cavity. An average of 98% to 99% of the tumor cells are removed. Fluorescent-guided resection is often employed for extracting out as much of the tumor tissue as possible with the goal of extending survival. Stummer et al., 2000, J. Neurosurg. 93:1000-1013. MRI-guided laser ablation is another means of resecting as much malignancy as possible. Kubben et al., 2011, The Lancet 12:1062-1070. Another method for locating glioblastoma cells prior to resection employs a non-fluorescent prodrug, 5-Aminolevulinic acid (5-ALA), that causes fluorescent porphyrins to aggregate in malignant glioma cells, which then become visible under blue light during a craniotomy. 5-ALA can be administered to glioblastoma patients intravenously or orally.

Resection is also often followed by post-operative stereotactic radiosurgery. C11 methionine positron emission tomography (MET-PET) imaging helps locate and target the remaining disease within the partially-collapsed surgical cavity. P. M. Wald, et al., International Journal of Radiation Oncology, Biology, Physics. Volume 96, Number 2S, Supplement 2016. Despite these procedures, glioblastoma cells survive or have already metastasized to locations beyond reach of the surgeon resulting in tumor regrowth. Since regrowth is rapid, chemotherapeutic treatment is usually immediate.

There have been no new chemotherapeutics capable of crossing the blood brain barrier (BBB) approved for glioblastoma in decades. Temozolomide, an agent that alkylates/methylates DNA, remains the most widely used and is taken during radiation therapy. Other agents include carmustine, a dialkylating agent, lomustine, an alkylating agent; vincristine, which binds to tubulin proteins, cisplatin, an alkylating agent, bevacizumab, an angiogenesis inhibitor, etoposide, an inhibitor of DNA topoisomerase II, and procarbazine, an alkylating agent. New or repurposed small molecules have not been developed in favor of biologics and devices capable of more precise targeting of radiation.

The blood-brain barrier (BBB) prevents most pharmaceutical compounds from crossing from the blood to the brain and only small molecules are capable of these feats. In addition to the BBB, glioblastomas form an additional barrier called the blood-brain tumor barrier (BBTB)) in the peripheral regions, creating a double barrier for drugs. Various drug transporters, and receptor-mediated drug delivery systems selectively enhance drug delivery and exploratory use of cell permeable tumor-targeting peptides on the surface of nanoparticles is underway. Dong X, Theranostics. 2018; 8(6): 1481-1493.

Among the class of drugs called monoclonal antibodies bevacizumab is used to prolong the time between initial treatment and tumor regrowth by activating the immune system to attack surviving glioma cells. Bevacizumab is delivered via intravenous infusion.

One experimental approach to treating glioblastoma cells post-surgically involves topical delivery of a chemotherapeutic on a biodegradable polylactic acid scaffold. It is believed that mesenchymal stem cells delivered into the surgical resection cavity on a polylactic acid scaffold will result in tumor killing. Sheets et al, "Image-Guided Resection of Glioblastoma and Intracranial Implantation of Therapeutic Stem Cell-seeded Scaffolds", J. of Visualized Experiments (July 2018). Other research supports the use of encapsulated therapeutic stem cells implanted in the tumor resection cavity to induce cell death in gliomas. Kauer et al, Nat Neurosci 15: 197-204.

The U.S. Food and Drug Administration has approved tumor-treating fields (TT Fields), a cap-like device which sends mild electrical charges through the skull to interfere with cancer cell division. The goal is to slow down a tumor's growth or metastatic rate while avoiding harm to normal cells. TT Fields is not a cure but has the advantage of avoiding the pain, nausea, fatigue, or diarrhea associated with chemotherapy and radiation.

Irradiated boron isotopes (also known as boron-neutron recapture) have been explored as a way of targeting glioblastomas for several decades. In recent clinical trials, patients with malignant glioblastoma treated with boron neutron recapture therapy in combination with standard radiation therapy survived significantly longer than those on standard therapy.

Coal Tar

Coal tar is made by heating coal in coke ovens to drive off volatile material. A description of the coking process can be found at the Cooper Creek Chemical Corporation website, under the reference titled "How is Crude Coal Tar Derived". Coal tar is a mixed compound composed primarily of polycyclic aromatic hydrocarbons, including phenanthrene, acenaphthene, fluorene, anthracene, and pyridine. Coal tar is insoluble in water but mostly dissolves in benzene, and partially dissolves in alcohol, ether, chloroform, acetone, carbon disulfide, chloroform, and methanol.

Virtually all commercially available coal tar is produced as a byproduct of the manufacture of blast furnace coke from coal. Modern coke ovens are based on the dry distillation of coal in large horizontal chambers. The chambers are built of ceramic materials to allow heating the coal to temperatures exceeding 1,100 degrees centigrade. This dry distillation causes the coal to decompose into gas, liquid (tar), and solid coke. Gas and tar are collected in a series of condensers and coolers and processed to yield certain articles of commerce and a dry fuel gas.

The liquid product, coal tar, contains a complex mixture of hydrocarbons and other compounds containing variously, oxygen, sulfur and nitrogen. The key characteristic of all these coal tar components is their highly aromatic chemical structure, which is the result of the high temperatures in the coke oven.

When coal tar is used as a medicament, the pitch (27% of coal tar) may be boiled off above 400 degrees centigrade and may be removed from the final medicament by the supplier. Gas chromatography or HPLC can be used to assure that the coal tar USP used for treating basal cell carcinoma or glioblastoma contains no pitch and matches established consistency standards.

Recovery of specific coal tar fractions is initially based on their boiling range and is carried out in standard commercial distillation equipment. Emphasis is normally placed on the following three fractions in order of boiling range:

1. The light oil, BTX fraction. This fraction contains mainly compounds with a single aromatic ring, i.e., benzene, toluene and xylenes, hence the term "BTX." The boiling points of these three compounds are, respectively, 80, 111, and 138-144 degrees centigrade.

2. The naphthalene fraction. This contains most of the valuable chemical naphthalene, boiling point 218 degrees centigrade.

3. Distillate fraction. This represents the remaining distillable fraction of the coal tar. The higher boiling non-distillable part, commonly referred to as pitch, is removed from the still as liquid. It usually represents more than half of the original tar.

The distillate fraction leaves the still as vapor from the top of the distillation tower and is condensed for recovery. The compounds which make up the main part of the distillate fraction are known as coal tar for medicinal purposes.

For further information concerning the above process, see the Kirk-Othmer Encyclopedia of Chemical Technology. 1997. New York: John Wiley & Sons, Inc. Volume 23. "Tars and Pitches."

As a quality control measure, various methods known in the art may be used to monitor and quantify the top 17 fractions from the distillate fraction (see Example 4). For example, using classic column chromatography to separate the 17 fractions, monitoring by thin layer chromatography (TLC) where the mobile phase or eluent is pure hexanes (for the first 15 fractions), ethyl acetate (for fraction 16), and methanol (for fraction 17).

Therapeutic Uses of Coal Tar

One coal tar solution for topical use is described at the Universal Preserva-A-Chem Inc. website, under the product "coal tar topical solution USP", where the chemical formula, properties, and some synonyms are listed. Coal tar solutions are often referred to as liquor carbonis detergens (LCD).

According to Wikipedia: "Coal tar was discovered around 1665 and used for medical purposes as early as the 1800s. It is on the World Health Organization's List of Essential Medicines, the most effective and safe medicines needed in a health system. Coal tar is available as a generic medication and over the counter. Coal-tar was one of the key starting materials for the early pharmaceutical industry."

Coal tar is available in the United States in a US pharmacopeia (USP) grade with a maximum residue on ignition of 2.0%. Coal tar ointment USP (obtained by combining coal tar with polysorbate 80 (a sorbitan mono-oleate polyoxyethylene derivative) and blending with zinc oxide paste) and coal tar topical solution USP (made by combining coal tar with polysorbate 80 and diluting with ethanol to an ethanol content of 81.0-86.0%) are also available in the United States.

Coal tar USP is approved for use in the United States in denatured alcohol, formula 38-B and 38-F. Numerous products, coal tar strengths, dosage forms, routes of administration and brand or generic forms are available. Coal tar USP is known to penetrate to the stratum germinativum.

Raw coal tar is known to pass through the blood brain barrier (BBB) and have neurological effects. The BBB protects the brain from noxious, electrically charged chemicals that circulate in the blood by preventing them from entering the brain. Therefore, to pass through the BBB, a pharmacologic agent should be non-polar.

The American Society of Health-System Pharmacists; Drug Information 2016. Bethesda, MID describes the well-established uses of coal tar products for dermatological conditions. Coal tar has been used in the management of dandruff, seborrheic dermatitis, and psoriasis, where it reduces the number and size of epidermal cells produced. This has led to the suggestion that coal tar extracts oxygen from the skin, thereby inhibiting cell reproduction (mitosis) and causing a decrease in the size and number of cells in the stratum germinativum and stratum corneum. Another suggestion is that coal tars formulated in various soaps and shampoos exert their therapeutic action in patients with dandruff, seborrheic dermatitis, or psoriasis by penetrating the epidermis and removing the scales produced by these skin disorders. Polyphenolic substances and peroxides in coal tar may react with epidermal sulfhydryl groups to produce an effect on skin that is similar to that resulting from exposure to sunlight. This effect could theoretically decrease epidermal proliferation and dermal infiltration.

Coal tar preparations are used topically alone or in combination with other drugs (e.g., salicylic acid or sulfur) for controlling dandruff, seborrheic dermatitis, or psoriasis. Although there are few well-controlled studies demonstrating their efficacy, coal tar preparations are used and generally considered effective for relieving the itching and scalp flaking associated with dandruff; for relieving the itching, irritation, and skin flaking associated with seborrheic dermatitis; and for relieving the itching, redness, and scaling associated with psoriasis.

A combination of coal tar components for the treatment of disorders responsive to dihydrofolate reductase (DHFR)-inhibition is disclosed in U.S. Pat. No. 6,337,337. DHFR catalyzes the NADPH-dependent reduction of 7,8-dihydrofolate (H2F) to 5,6,7,8-tetrahydrofolate (H4F) and is necessary for maintaining intracellular levels of H4F, an essential cofactor in the synthetic pathway of purines, thymidylate, and several amino acids. The inventive coal tar compositions described in the '337 patent are believed to inhibit the transfer of the hydrogen ion on NADPH to dihydrofolate reductase, thus preventing metabolism within the nucleus of tetrahydrofolate. Because neoplastic cells are more responsive than slower-dividing normal cells to this resulting interference with DNA synthesis, repair, and cellular replication, cancers responsive to antifolate therapy as delineated in the '337 patent do not divide and are known to "explode" upon treatment with coal tar products. The '337 patent describes compositions of coal tar as functionally replicating the antifolate methotrexate for the treatment of certain cancers.

Toxicity of Coal Tar

A comprehensive review of the toxicity of coal tar by the U.S. Department of Health and Human Services appeared in 2002 and can be found in the creosote toxicology profile found at the Agency for Toxic Substances and Disease Registry's website. The document reviews studies that provided mixed evidence as to whether coal tar causes squamous cell carcinoma and other tumors. Much of the research reviewed concerned long-term occupational exposure in the air or in the factory, often decades in the past, when industrial standards of hygiene and worker safety were not as strict as at present. Furthermore, where evidence of tumorigenicity was purportedly found, the effects observed may have required a combination of chronic exposure to coal tar or its products and exposure to sunlight.

Notably, studies did not find a statistical correlation between the use of coal tar products on human skin and cancer incidence. Perhaps the best data on human coal tar use came from users of coal tar for psoriasis. In particular, a study by Bhate et al., summarized on page 136 of the government review, used a large population, was placebo controlled, and the cancers sought were extensive. The study found that the incidence of cancer (total, skin, breast, cervix, genitourinary tract, bronchus, gastrointestinal tract, lymphoma, or other) was not significantly greater in 2,247 patients with psoriasis than in 4,494 age-matched controls without psoriasis.

In other studies, reproductive risks in humans were not found, and despite many reported studies in the review, none could identify a biological risk of any significance to humans (other than benign tar warts among creosote tar workers with 5 to 40-year exposures), including to the central nervous system.

There were also studies that examined the effects of some of the constituents of coal tar (as opposed to the effects of coal tar as a whole). Although some of the studies reviewed would be considered inadequate by current standards, the results nevertheless indicate that coal tar creosote and its constituents can induce skin tumors as well as act as tumor initiators and promoters. Nevertheless, the International Agency for Research on Cancer, the American Conference of Governmental Industrial Hygienists, the National Toxicology Program, and the Occupational Safety and Health Administration reported that no component of coal tar present at levels greater than or equal to 0.1% is identified as a probable or confirmed human carcinogen.

SUMMARY OF THE INVENTION

Provided herein are methods of treating basal cell carcinoma or glioblastoma comprising administering to a patient in need thereof a therapeutically effective amount of a coal tar product. In some embodiments, the coal tar product is coal tar USP, coal tar ointment USP, or coal tar topical solution USP. In some embodiments, the coal tar product is applied topically to a basal cell carcinoma. In some embodiments, the coal tar product is present in a pharmaceutical composition.

Also provided herein are methods of treating basal cell carcinoma or glioblastoma that comprise administering a coal tar product to a patient in need thereof in combination with another therapeutic treatment that is effective to treat basal cell carcinoma or glioblastoma. In some embodiments, the other therapeutic treatment is a treatment for basal cell carcinoma or glioblastoma is surgical excision, curettage and electrodessication, Mohs micrographic surgery, radiation, cryosurgery, photodynamic therapy, laser surgery, imiquimod, 5-fluorouracil, vismodegib, or sonidegib. In some embodiments, the treatment is a treatment for glioblastoma and used alone or in combination with surgical removal, radiation, chemotherapy, tumor treating fields, bevacizumab, polylactic acid or similar scaffolding or encapsulation.

Current treatment of basal cell carcinoma usually requires surgical removal as cells in the basal layer are not completely killed by current topical treatments. This generally leads to scarring at the surgical site. Surprisingly, unlike current topical treatments, coal tar products penetrate to the basal layer and kill neoplastic basal cell carcinoma cells capable of metastasis. Thus, following coal tar product treatment, the remains of the basal cell carcinoma or glioblastoma may be simply frozen off, leaving the skin in pristine condition once the epidermis heals.

As an alternative to cryotherapy, the remaining basal cell carcinoma may be scraped off (curettage) by a medical professional, similar to the current method of removing actinic keratoses. The benefit of cryotherapy or curettage is faster removal and recovery to a normal appearance.

In some embodiments, the coal tar product is administered before the other therapeutic treatment. In some embodiments, the coal tar product is administered after the other therapeutic treatment. In some embodiments, the coal tar product is administered at the same time as the other therapeutic treatment.

In some embodiments, the coal tar product and the other therapeutic treatment are administered together, in a single pharmaceutical composition. In some embodiments, the coal tar product and the other therapeutic treatment are administered separately, in different pharmaceutical compositions. In some embodiments, the coal tar product is administered topically or as a therapeutic dressing to the lining of a post-surgical cavity and the other therapeutic treatment is administered with a device (e.g. gamma knife), topically, orally, intravenously, or subcutaneously. In some embodiments, the coal tar product is administered intravenously, and the other therapeutic treatment is administered with a device (gamma knife), topically, orally, intravenously, or subcutaneously.

Following treatment with a coal tar product and, optionally, another therapeutic treatment, daily or frequent (e.g., 1× weekly, 2× weekly, 3× weekly, 4× weekly) application of a low concentration of a coal tar product (e.g., coal tar USP as a 0.1% to 0.5% alcohol solution) by the patient to the affected area is advised to prevent or delay recurrence of the basal cell carcinoma.

Before or following removal of a glioblastoma, and, optionally, another therapeutic treatment, application to the surgical cavity prior to closure of a coal tar product (e.g., coal tar USP at 0.00005% to 0.5% in an ethanol, lactic acid, or dipropylene glycol (DiPG) solution, or in a mixture comprising 50% DMSO, 35% PEG 400 and 15% ethanol and excipients, or incorporated into a delivery vehicle such as a polylactic acid scaffold). See FIG. 2.

Thus, disclosed herein is a method of preventing basal cell carcinoma comprising administering to a patient who previously was treated for basal carcinoma a therapeutically effective amount of a coal tar product. In some embodiments, the coal tar product is administered to an area of the patient's skin where a basal cell carcinoma previously appeared and was treated, and the method prevents the recurrence of the basal cell carcinoma. In some embodiments, the coal tar product is administered to an area of the patient's skin near (within about one or two inches) where a basal cell carcinoma previously appeared and was treated, and the method prevents the appearance of a new basal cell carcinoma.

DETAILED DESCRIPTION OF THE INVENTION

"Administering" refers to providing a coal tar product or a pharmaceutical composition comprising a coal tar product to a patient in need thereof by any means known in the pharmaceutical art and includes self-administration by the patient as well as administration by a physician or other health care provider. "Administering" includes local delivery of a coal tar product directly into or onto a target tissue (such as topical administration to a basal cell carcinoma or injection into a basal cell carcinoma or topical delivery to the lining of a surgical cavity after brain tumor removal).

"Coal tar product" refers to a therapeutic agent derived from coal tar. In some embodiments, the coal tar product has efficacy in treating basal cell carcinoma. In some embodiments, the coal tar product has efficacy in treating glioblastoma. Examples of "coal tar products" include coal tar USP, coal tar topical solution USP, and coal tar ointment USP.

"Patient" preferably refers to a human but may also refer to companion animals such as dogs or cats, or farm animals such as horses, cattle, pigs, or sheep.

"Pharmaceutically acceptable" refers to a carrier, diluent, or excipient that is compatible with the other ingredients of a formulation and is not deleterious to the patient to whom the formulation is administered.

"Therapeutically effective amount" refers to an amount of coal tar product that results in a desired change in the physiology of the patient to which a coal tar product is administered, e.g., a reduction in the size of a basal cell carcinoma or a glioblastoma.

Surprisingly, coal tar USP in a pharmaceutically acceptable carrier has been found to be effective against cancers not responsive to antifolate therapy such as methotrexate. In particular, and unexpectedly, coal tar USP in an acceptable pharmaceutical carrier is shown to be effective for topically treating basal cell carcinomas. Basal cell carcinomas are currently often treated with the Mohs surgical method of slicing contiguous layers of skin until no additional cancer cells are observed through high magnification in the sample slice. This method, however, is not a cure and recidivism is common. A chemical bathing of the basal layer with a coal tar product derived anti-cancer agent such as disclosed herein offers a more complete and less disfiguring therapy to the patient. Furthermore, low-dose follow-up application has been shown to prevent recurrence in the immediate area and in the broader proximity to the initially-treated basal carcinoma.

Figure 1:
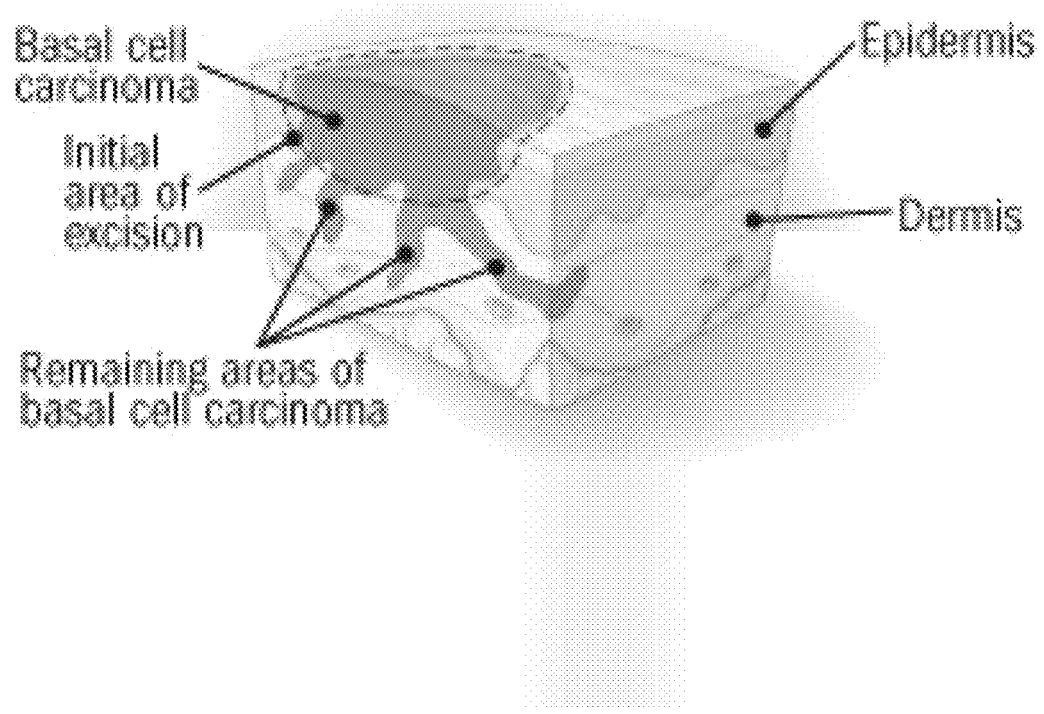
FIG. 1 shows a schematic depiction of a basal cell carcinoma and typical incision for surgical removal.
Figure 2:
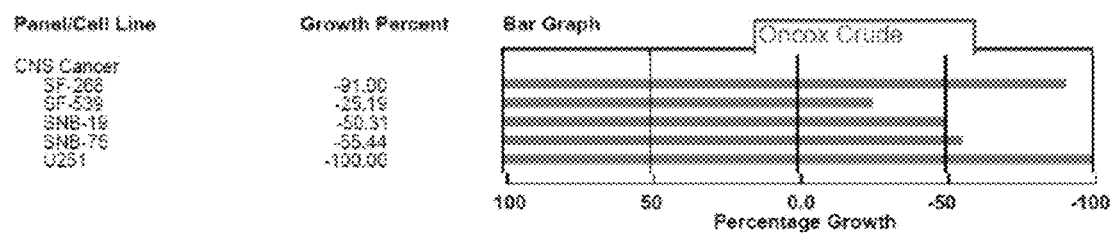
FIG. 2 shows the growth inhibition bar graph of assays conducted at the U.S. National Cancer Institute of a composition derived from coal tar (see Example 4) on the CNS cancer cell lines glioblastoma SF-268 and astrocytoma U251.

Equally surprising, coal tar USP in an acceptable pharmaceutical carrier at a concentration of 100 µg/ml inhibited the growth in vitro of glioblastoma multiforme cells (U251, a grade IV astrocytoma) by 100% and astrocytoma cells (SF-268 cell line) by 91% in assays completed at the U.S. National Cancer Institute (NCI). See FIG. 2. The use of a coal tar based therapeutic in each cancer offers a preferable method of treatment over surgical resection, which is rarely a cure as some cancerous cells remain behind, regrow, or metastasize.

Optionally, if surgical removal of the tumor is recommended, topical use of a coal tar based therapeutic to the lining of the surgical cavity after tumor resection, alone or in combination with other medicaments or treatments, provides additional cell-kill of glioblastoma multiforme cells that are beyond the reach of surgical instruments or left in place due to proximity to critically functional neurons, such as speech.

While not intending to be bound by theory, one possible explanation for the effectiveness of coal tar products in treating glioblastoma is based on their non-competitive binding, electron transport, or allosteric effect on NADPH. Neoplastic cells are more responsive than slower dividing normal cells to this resulting interference with DNA synthesis, repair, and cellular replication that results from NADPH hydrogen-transfer inhibition.

Moreover, tumorigenic cells generally require higher levels of NADPH than wild-type cells due to, e.g., their greater mitotic activity and need for anti-oxidative functions, particularly during chemotherapeutic or radiation therapy. NADPH is used by glioblastomas to survive radiation treatments by increasing production of deoxynucleotides and antioxidants, specifically glutathione and thioredoxin, which help reduce oxidative stress after radiation and repair radiation-induced DNA damage. Inhibiting the production of enzymes producing NADPH resulted in greater sensitivity by glioblastomas to both in vitro and in vivo radiation. See Spitz et al., 2004, Cancer Metastasis Reviews 23:311-322.

Inhibiting NADPH production could potentiate the effectiveness of radiation therapy of glioblastoma since glioblastomas differ from surrounding normal tissue with respect to NADPH metabolism and inhibition of the NADPH-producing enzyme isocitrate dehydrogenase 1 (IDH1) sensitizes glioblastomas to radiation in vitro and in vivo by inducing NADPH-dependent cellular senescence. Temozolide, the primary radiosensitizer currently in use, has only modest efficacy. Although it is widely used in combination with surgery and radiation, most glioblastoma patients still die due to recurrences within the high dose radiation field. Wahl et al., 2017, Cancer Res. 77:960-970.

Accordingly, disclosed herein is a method of sensitizing glioblastoma to radiation treatment by inhibiting or interfering with the reducing-capacity of NADPH comprising administering to a patient having glioblastoma a therapeutically effective amount of a coal tar product. In some embodiments, the patient is then administered a therapeutically effective dose of radiation at the same time as or after being administered the coal tar product.

In some embodiments, the methods of treating basal cell carcinoma disclosed herein eliminate the need for surgical removal of basal cell carcinoma growths and the risk to adjacent skin when chemotherapeutic ointments or creams are used. The medicaments disclosed herein are not harmful to normal skin and attack and kill only basal cell carcinoma cells.

Combination drugs are generally more effective than single-molecule drugs, since malignant cells often can cope when exposed to one chemical, but when two or more are put together, the therapeutic response is generally stronger and often enough to stop cell growth and induce tumor cell death. Coal tar USP, being a combination of many molecules in one drug, has the benefit of overwhelming the defenses malignant cells use to become drug resistant.

The efficacy of coal tar described herein on two tumor types that are not responsive to dihydrofolate reductase (DHFR) inhibition—basal cell carcinoma and glioblastoma—is surprising in view of the teachings of U.S. Pat. No. 6,337,337, which discloses the antitumor effects of coal tar products as arising via a mechanism similar to that of DHFR.

Pharmaceutical Compositions

When the coal tar products disclosed herein are administered as pharmaceuticals to humans or animals, they are generally given as a pharmaceutical composition containing, for example, about 0.00005 to 3%, about 0.001 to 2.5%, about 0.5 to 2%, or about 1 to 1.75% (w/w, w/v, or v/v) of coal tar product in combination with one or more pharmaceutically acceptable carriers. In some embodiments, the pharmaceutical composition contains about 0.00005%, about 0.001%, about 0.01%, about 0.03%, about 0.05%, about 0.075%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2% (w/w, w/v, or v/v) of coal tar product in combination with one or more pharmaceutically acceptable carriers.

In some embodiments, the pharmaceutical composition comprises coal tar USP at about 2% wt/wt diluted in DMSO, ethanol, or dipropylene glycol (DiPG).

Dosage levels of the coal tar products in the pharmaceutical compositions may be varied so as to obtain an amount of the coal tar product which achieves the desired therapeutic response for a particular patient and mode of administration, without being toxic to the patient.

The dosage level will depend upon a variety of factors, including the activity of the particular coal tar product, the route of administration, the time of administration, the rate of excretion or metabolism of the coal tar product, the rate and extent of absorption, the duration of the treatment, whether other drugs are also being administered to the patient, the age, sex, weight, condition, general health, and prior medical history of the patient being treated, and like factors well known in the medical arts.

In general, a suitable daily dose of a coal tar product disclosed herein will be that amount of the coal tar product which is the lowest dose effective to produce a therapeutic effect. Such an effective dose will usually depend upon the factors described above. Generally, oral, intravenous, and subcutaneous doses of the coal tar product for a patient will range from about 0.0001 to about 200 mg, or about 0.001 to about 100 mg, or about 0.01 to about 100 mg, or about 0.1 to about 100 mg, or about 1 to about 50 mg per kilogram of body weight of the patient per day.

The coal tar products can be administered as a single dose, daily, once a day, twice a day, three times a day, or more. Other schedules include every other day, three times a week, twice a week, weekly, or bi-weekly. The dosing schedule can include a "drug holiday," i.e., a period of time when the coal tar product is not administered. For example, the coal tar product can be administered for two weeks on, one week off, or three weeks on, one week off, or four weeks on, one week off, etc., or continuously, without a drug holiday. The coal tar products can be administered orally, intravenously, intraperitoneally, topically, transdermally, intramuscularly, subcutaneously, intranasally, sublingually, by inhalation, or by any other route.

In order to produce pharmaceutical compositions, coal tar products are generally dissolved in solvents. Some coal tar solvents are composed of neutral, acidic, or basic cyclic compounds characterized by the presence of a six-membered ring in the molecule and most are soluble with each other. Coal tar USP is only slightly soluble in water and partially soluble in acetone, alcohol, carbon disulfide, chloroform, ether, and methanol. These solvents may be used alone or in combinations. Moreover, solvents in addition to those mentioned above may be used.

For use on basal cell carcinoma requiring delivery to the basal layer, a preferred solvent system for coal tar USP is a mixture of ethanol (IPA 99%), dipropylene glycol (DiPG), PEG 400 monostearate and acetic acid. The preferred ratio is 48-50% ethanol, 30% DiPG, 15% PEG 400 and 3-5% acetic acid. Any remnant pitch (or solutes) will precipitate immediately or within 24 hours after mixing and will adhere to plastic containers or can be filtered out through a porous membrane.

Dipropylene glycol, chemical formula $C_6H_{14}O_3$, is a mixture of three isomeric chemical compounds, 4-oxa-2,6-heptandiol; 2-propan-1-ol; and 2-propan-1-ol. It is a colorless, nearly odorless liquid with low toxicity and a molar mass of 134.173 g/mol. Dipropylene glycol is commonly used in pharmaceutical formulations as it is miscible with water and soluble in ethanol.

It is well known that DiPG is a skin penetrant and one of the preferred diluents for the delivery of topical drugs to the skin. The MSDS for DiPG can be found in the Environmental Working Group's cosmetics database website. A minimal amount of acetic acid in the solvent mixture will help soften and exfoliate the corneocytes in the stratum corneum where lipids in these cells can otherwise trap the medicament.

Other solvents or partial solvents of the polycyclic aromatic hydrocarbons found in coal tar USP are isopropyl myristate, PEG 600, Cremophor® EL PEG-35 Castor Oil, ethanoic acid (aqueous acetic acid), avocado oil, sesame oil, tocopherol oil (Vitamin E), and castor oil. Other more exotic oils may also serve as either solvents or odor-masking diluents, including clove leaf oil, oil of rosemary, geranium Egyptian oil, oil of lemon and oil of juniper berry. These solvents and diluents can be used alone or in combination with other solvents.

For delivery of coal tar USP to a basal cell carcinoma, xanthan (from, e.g., CP Kelco) or guar gum may be added to an aqueous formulation at a concentration of approximately 0.5% to approximately 2.5% by first wetting the gum for at least one hour in one or more of oily solvents or fragrances, then adding this mixture to the coal tar USP solution and mixing together at a speed sufficient to create a vortex for 45 to 60 minutes. This will produce a gel consistency and allow the medicament to remain in place on the basal cell carcinoma, which is especially useful when treating basal cell carcinoma above the eyes or at the hairline where run-off might otherwise occur. A lower amount of xanthan gum (<0.5%) may also be added to a maintenance-level formulation (e.g., 0.1% coal tar USP) to increase adherence to the skin on the forehead and elsewhere.

Technologies and methods for topical delivery of coal tar products to basal cell carcinomas include unit dosing dispensing devices, needle, microneedle, non-needle injection devices, prefilled applicators such as infused pads, saturated wipes, adhesive bandages or tabs, creams, gels, and ointments, including petrolatum-based ointments.

A preferred method of topical delivery of a coal tar product to a basal cell carcinoma is to simply apply the coal tar product by hand to the basal cell carcinoma. In this embodiment, the coal tar product is preferably in a cream, ointment, lotion, or other similar form, and is placed upon the basal cell carcinoma, avoiding the surrounding normal tissue to the extent possible. Either the patient or a health care provider may apply the coal tar product to the basal cell carcinoma. The amount of cream, ointment, lotion of other form of product applied will depend on the size and/or location of the basal cell carcinoma and will be readily ascertained by the patient or healthcare provider who applies the coal tar product.

In some embodiments, the coal tar product is allowed to remain at the site of application on the basal cell carcinoma. That is, it is not wiped off or otherwise removed after a certain period of time. However, in some instances, it may be desirable to wipe off the coal tar product after a certain period of time, e.g., 15 minutes, 30 minutes, 45 minutes, one hour, two hours, three hours, four hours, five hours, six hours, seven hours, eight hours, nine hours, ten hours, or longer.

In some embodiments, the coal tar product is applied to the basal cell carcinoma with a foam or cotton pad. In some embodiments, the coal tar product is applied with a bandage to seal the ointment, cream, or other topical delivery composition against the basal cell carcinoma. The length of time the bandage is left on depends on various factors such as the dose of coal tar product being applied and the nature (e.g., size, location) of the basal cell carcinoma.

Delivery to Central Nervous System (CNS) Tumors

In general, drugs that pass through the blood brain barrier (BBB) are small, non-polar, lipid-soluble molecules that permeate via diffusion. Permeability depends on many factors (molecule shape, flexibility, surface area, etc.) but two of the main characteristics that influence permeability are size and solubility. The molecular weight threshold for permeability is around 400 Da. Coal tar USP (with pitch removed) weighs 210-250 Da. In terms of the solubility threshold, if a drug forms less than 7 hydrogen bonds with water, there's a higher chance that it will pass the BBB. Coal tar USP is only slightly soluble in water and more soluble in lipids.

A discussion of the BBB and methods to overcome it can be found at the Quora website, under the question "What is the mechanism which allows drugs to pass across the blood brain barrier?" as answered by Jens Mowatt. A summary of the characteristics of drugs that pass through the BBB is found in Pardrige, 2012, J. Cereb. Blood Flow. Metab. 32:1959-1972.

Once a drug passes through the BBB, it has to partition into an aqueous environment. To assure that coal tar USP retains its integrity in this aqueous environment, coal tar USP may be formulated with the solvent dipropylene glycol, a lipid, and optionally an alcohol to maintain hydrophobicity for passage through the BBB and, once in the brain, a low lipid content to avoid uptake by peripheral tissue and loss of drug characterization or dosage.

For delivery to the brain, long-lasting nano-injectables, including liposomes, polymeric nanoparticles, nanocrystals, microspheres, drug-implanted polymers, and antibody drug conjugates are preferred. Transmucosal delivery, inhalation, and oral formulations are also preferred. Such non-invasive methods of delivery of coal tar USP are preferred over injection due to the difficulty in locating the nucleus of the glioblastoma tumor as it winds its tentacles around the nerves. Unless the center of the tumor is located, injection treatments are ineffective. It is anticipated that coal tar USP delivered by inhalation or through the mucosal tissue of the nose will be effective as some antibiotics with true benzene rings are used to treat CNS infection and pass through the blood brain barrier. These include isoniazid, pyrazinamide, linezolid, fluconazole, and fluoroquinolone. Additionally, one of the dominant compounds in coal tar USP, quinoline, passes through the blood brain barrier via passive diffusion.

As an alternative to encapsulation with a non-polar coating, drug delivery of coal tar products to glioblastomas through the blood stream and the blood brain barrier can be achieved by removing any electrically-charged particles from coal tar as described in U.S. Pat. No. 5,354,475.

Coal tar products also may be injected or surgically implanted directly into the brain in order to treat glioblastomas. This approach has the advantage of reducing the side effects of any interactions of the coal tar product with other tissues or organs. One possibility is to use an implantable, slow-dissolving polymer wafer containing the coal tar product. Such a slow-dissolving polymer wafer containing carmustine (GLIADEL®) has been approved by the U.S. Food and Drug Administration for treating glioblastoma and may be adapted by those skilled in the art to deliver coal tar products to glioblastomas. See Perry, et al., 2007, Curr. Oncol. 14:189-194, for a discussion of GLIADEL®.

Nasal administration of medication for the treatment of neurodegenerative diseases has proven to be a way to bypass the blood brain barrier including large, polar molecules via olfactory and trigeminal nerves, despite some issues around irregular drug absorption, variation in absorption in different regions of the brain, and nasal congestion. Drugs currently delivered intranasally include anti-migraine drugs like IMITREX® (sumatriptan), ZOMIG® (zolmitriptan), MIGRANAL® (dihydroergotamine), and SINOL-M®. More examples include peptide drugs (used for hormone treatments and given intranasally to avoid drug degradation after oral administration) such as desmopressin. Synctocinon can be given intranasally to increase duration and strength of contractions during labor. Intranasal calcitonin is given for a variety of conditions and intranasal midazlolam is used for seizure episodes in children. Investigations also show that intranasal naloxone for opiate overdoses can be just as effective as by injection. Additionally, many recreational drugs are taken intranasally.

Drug delivery via the lungs is an effective way not only for local but also for systemic treatment. In general, the lungs are permeable to both smaller molecules and larger macromolecules, as well as lipophilic and water-soluble small molecules. The benzenes in coal tar USP enter the bloodstream via respiratory pathways. Several compounds also found in coal tar USP, namely pyrene (see U.S. Patent Application Publication No. US 2009/0238754 and International Patent Publication WO 2009/117042) and napththalene (see Freed et al, 2002, Peptides 23:157-65) traverse the blood brain barrier. Seizures are also treated with medicines delivered through the lungs, including STACCATO®, an epilepsy drug in clinical trials from Engage Therapeutics.

Post-surgical delivery of a coal tar product to the cavity bed of an excised tumor offers another method of reducing tumor regrowth and metastasis and extending longevity.

Additional Delivery Methods

Various other methods known in the art may be used to deliver coal tar products for use in the methods of therapy described herein.

For example, liposomal delivery is a well-established means of delivering drugs, particular drugs used to treat cancer. See, e.g., Drummond et al., 1999, Pharmacol. Rev. 51:691-743. Liposomes are non-toxic, biodegradable and may provide better solubility and stability as well as slower release of drugs, as opposed to free administration. A recent variation of liposomal technology that may be employed in the methods described herein are the cell-penetrating peptide amphiphile integrated liposomal systems for enhanced delivery of anticancer drugs to tumor cells described in Sardan et al., 2013, Faraday Discuss 166:269-83.

Another possible method of delivering coal tar products is via microneedle patches, which are arrays of needles measuring hundreds of microns in length that can deliver medication into the skin in a pain-free and simple manner. See, e.g., Prausnitz, 2017, Ann. Rev. Chem. Biomol. Eng. 8:177-200.

Transdermal patches are also a possible delivery method and provide for the movement of drugs across the skin for absorption into the systemic circulation, relying on either passive means that do not disrupt the stratum corneum or active means which do. See, e.g., Pastore et al., 2015, Br. J. Pharmacol. 172:2179-209.

Excipients known to be compatible with normal brain tissue function as diluents, solvents, penetration enhancers and time-release agents to maximize the benefit of the coal tar product.

EXAMPLES

Example 1—Treatment of Basal Cell Carcinomas on Human Skin

Figure 3A:
FIG. 3A-C shows basal cell carcinoma on the forehead of a patient prior to first treatment (see Example 1). A, before treatment; B, during treatment; C, after treatment.
Figure 3B:
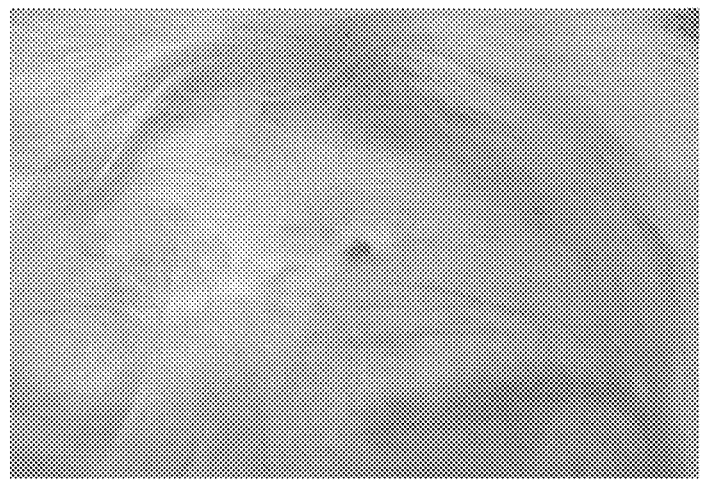
Figure 3C:

An ointment consisting of 95% petrolatum and 5% coal tar solution USP (see U.S. Pat. No. 6,337,337 and Example 4 below) was applied 2× day for 13 days to a basal cell carcinoma on the forehead of a human female. Shown in FIGS. 3 A, B, and C is the BCC before, during, and after treatment, respectively.

Figure 4A:
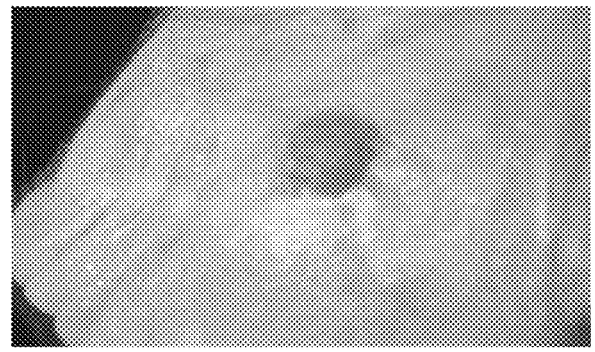
FIG. 4A-C shows a basal cell carcinoma on the right forehead of the same patient that occurred four years after the basal cell carcinoma of FIG. 3A-C was treated. A, before treatment; B, during treatment; C, after treatment. See Example 1.

Four years later, the same patient was treated for basal cell carcinoma on the right forehead. Treatment consisted of twice daily applications for 10 days of a liquid solution containing refined coal tar (Koppers, Inc., Pittsburgh, Pa., brand NSR, Stickney Plant, LDO #2006-0566, Sample 06-244) in 65% ethanol and 35% Polyethylene glycol (PEG) 400 v/v at a concentration of about 2%. Listed in Table 110 are the compounds found in the Koppers coal tar product sold to industry for dandruff shampoo manufacturing. This treatment was combined with cryotherapy using liquid nitrogen to freeze off the basal cell carcinoma. The results of the treatment are shown in FIGS. 4A (before treatment) and 4B (after treatment). On the day of the last treatment, and just before removal, the tumor was seen to be scaling and starting to flake.

Figure 5A:
FIG. 5A-B shows two basal cell carcinomas on the right and left forehead of the same patient that occurred four years after the basal cell carcinoma of FIG. 4A-B was treated. See Example 1. Before and after photos of the left and right basal cell carcinoma are shown in 5A (before treatment with coal tar USP) and 5B (after treatment with coal tar USP).
Figure 6A:
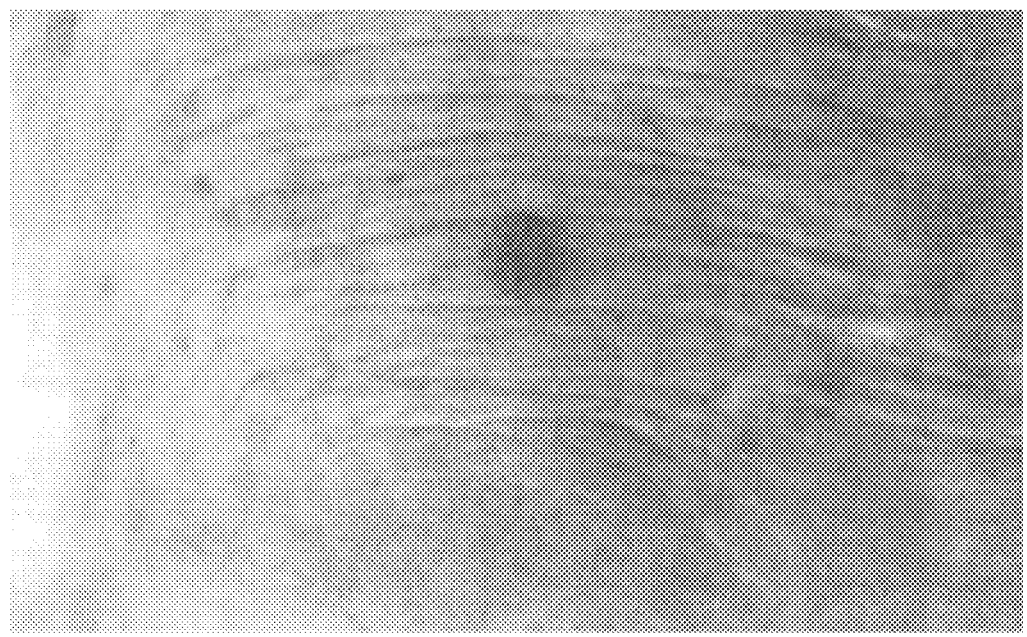
FIG. 6A-B shows a close up of the basal cell carcinoma on the patient's right forehead before (A) and after (B) four months of daily topical treatment and after eventual cryotherapy. The arrow and circled area in 6B indicate the location of the basal cell carcinoma.
Figure 6B:
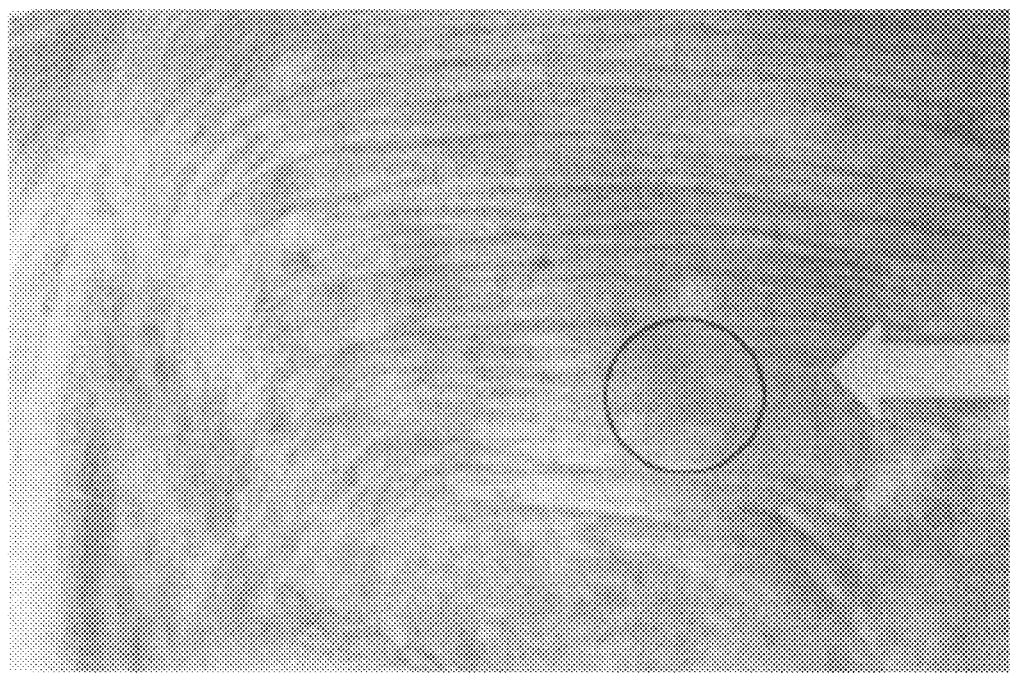

A third treatment of the same patient occurred four years after the second treatment when two basal cell carcinomas appeared on the same subject's forehead, one on the left side and one on the right side. During the intervening period_no treatment of the forehead occurred. Two coal tar USP formulations were used to shrink these basal cell carcinomas: Coal tar USP (Spectrum Chemical; CAS Number: 8007-45-2; available through VWR's website under "Coal tar USP") was combined with a mixture of 120 grain vinegar (Fleischmann's, 12% acetic acid) and grapeseed oil (Columbus Foods) as shown in the formula of Table 3 and applied 2× day. The second formulation using the same Spectrum Coal tar USP was also applied to both basal cell carcinomas 2× daily. This second formulation is also encompassed by Table 3. The basal cell carcinoma shrunk by about 50% on the right forehead above the right eye prior to cryotherapy. The basal cell carcinoma on the left side also shrunk about 50%. Before and after photos of the left basal cell carcinoma are shown in FIG. 5A (before treatment with coal tar USP), 5B (after treatment with coal tar USP). FIGS. 6A and 6B shows both basal cell carcinomas on the left and right side of the patient's forehead before treatment and upon completion of the topical coal tar treatments when cryotherapy removed the remaining basal cell carcinoma on the right side.

FIGS. 6A and B shows a close up of the basal cell carcinoma on the patient's right forehead before (A) and after (B) four months of daily topical treatment and after eventual cryotherapy as described in the paragraph above.

Figure 4B:
Figure 4C:
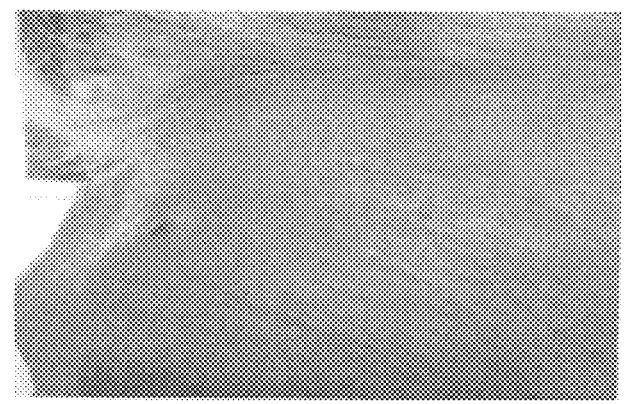
Figure 5B:
Figure 7A:
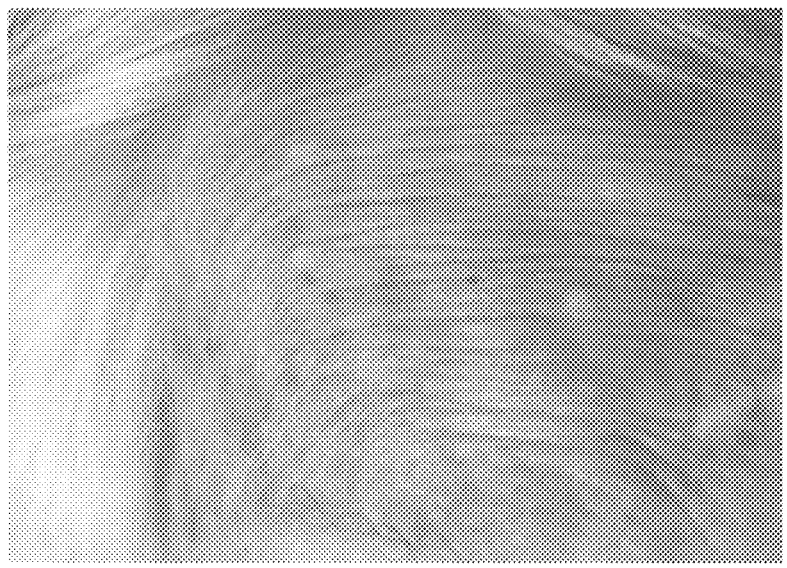
FIG. 7A-B shows the right side and center of the patient's forehead where large basal cell carcinomas appeared four years and one year previous to the time the photo was taken. See Example 1. A, area after preventative treatment 1 to 2 times daily with 0.1% coal tar USP dissolved in alcohol applied via cotton balls since the last basal cell carcinoma was removed. B, close up of the far-right side portion of A.
Figure 7B:
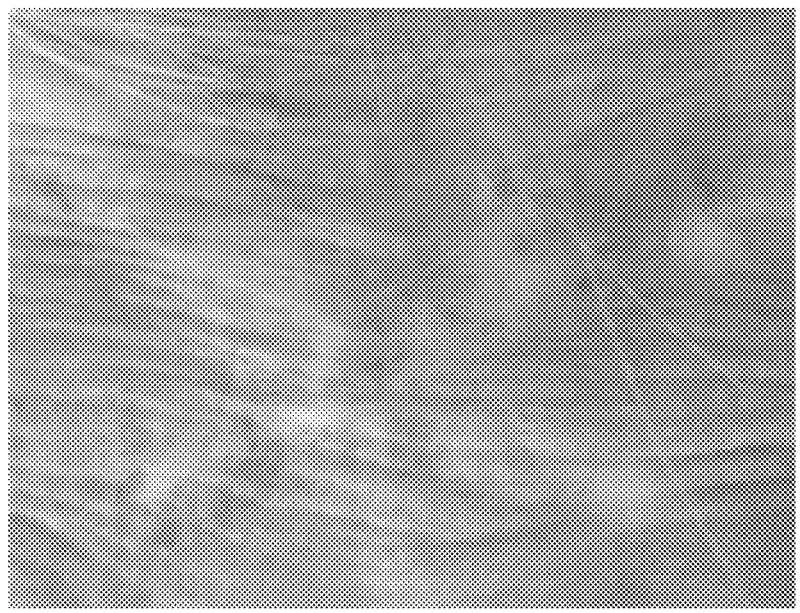

FIG. 7A shows the right side and center of the patient's forehead where large basal cell carcinomas appeared four years ago (FIG. 4) and again, one year ago (FIG. 5). Following removal of the last basal cell carcinomas, this area has been treated 1 to 2 times daily with 0.1% coal tar USP dissolved in alcohol applied via cotton balls and no new basal cell carcinomas have developed. FIG. 7B is a close up of a portion of FIG. 7A, with the white areas being scars from prior surgeries for the removal of basal cell carcinomas.

Figure 9A:
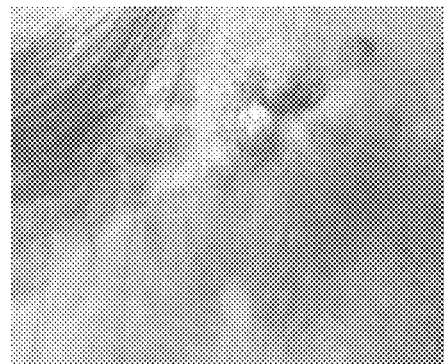
FIG. 9A-C shows before (A), during (B) and after (C) photos of a basal carcinoma that appeared from blemished skin on the patient's forehead and was treated 2× daily for 12 days (B) and then an additional 14 days (C) with the composition of Table 12 in Example 4.
Figure 9B:
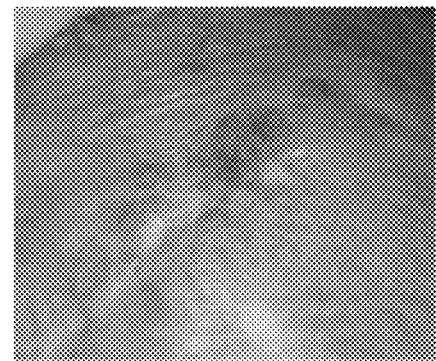
Figure 9C:
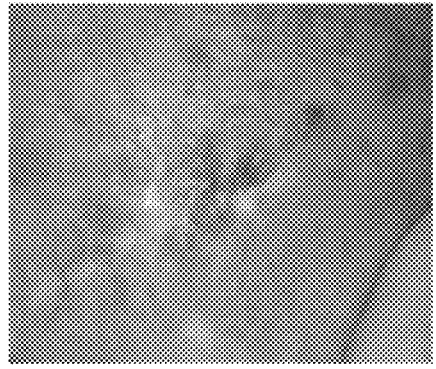

The patient had a purple blotch on her center forehead for six months which eventually produced a new basal cell carcinoma (see FIG. 9A). At that point, the composition of Table 12 in Example 4 was applied 2× daily for 21 days, at which point the cyst had flattened, desiccated and contracted in diameter (see FIG. 9B).

Example 2—Treatment of Astrocytomas and Glioblastoma Multiforme

Currently, dihydrofolate reductase (DHFR) inhibitors are not being used or clinically studied for the treatment of astrocytomas or glioblastomas. It is therefore surprising that coal tar USP would be effective in killing two cell lines of these brain cancers, SF-268 and U-251. However, studies done at the U.S. National Cancer Institute showed that a coal tar product (see Example 4 below) inhibited the growth in vitro of glioblastoma multiforme cells (U251, a grade IV astrocytoma) by 100% and astrocytoma cells (SF-268 cell line) by 91%. See FIG. 2.

Example 3—Formulations

TABLE 1

| Ingredient | Concentration (v/v) |
| --- | --- |
| Coal tar USP | 0.005 to 2% |
| DiPG | 1% to 15% |
| One or more lipids, preferably grapeseed oil or castor oil | 2% to 5% |
| Water | to 100% |

This formulation is suitable for intravenous infusion and may be used at a dose and schedule of 10 mg/kg to 15 mg/kg every 2-3 weeks. Other routes of injection may also be used, e.g., intramuscular, subcutaneous, or intraperitoneal.

Another formulation is shown below. In this formulation, water is used in combination with xanthan gum to make a gel. To mask the odor of coal tar USP, a de minimus amount of wintergreen oil (for example 0.025%) or 1% to 2% of a vanilla, flower-scented or similar pleasant fragrance oil can be added. This formulation is suitable for topical administration.

TABLE 2

| Ingredient | % of formulation (v/v) | Function |
| --- | --- | --- |
| Castor oil | 25 | solvent |
| Denatured alcohol | 25 | solvent |
| Coal tar USP | 2 | active ingredient |
| Xanthan gum | 1.6 | thickener, masker |
| Wintergreen oil | 0.025 | fragrance |
| Deionized water | 46.375 | diluent |

Another formulation contains aqueous acetic acid in the form of white vinegar (120 grain or 12% acetic acid) and grapeseed oil to create an oil/water emulsion which must be shaken before application to the skin. This formulation was used in the treatment of basal cell carcinoma on the patient disclosed in Example 1 above.

TABLE 3

| Ingredient | Weight (grams) | Percent of formulation |
| --- | --- | --- |
| Aqueous 12% acetic acid | 9.6 | 27.7 |
| Grapeseed oil | 24.5 | 70.6 |
| Coal tar USP | 0.6 | 1.7 |
| Totals | 34.7 | 100 |

The formulation in Table 3 was prepared as follows:
1. The aqueous 12% acetic acid and grapeseed oil were added to a mixing vessel and stirred on low for 15 minutes.
2. The coal tar was added to the mixing vessel and stirring at medium speed was carried out for 45 minutes, creating a small vortex.
3. The mixture was run through a homogenizer and filtered to remove particulates.

Hexane is not to be used in this formulation due to suspected damage to the central nervous system.

In one embodiment of the formulation of Table 3, the suppliers of the ingredients were as follows:

TABLE 4

| | |
|---|---|
| aqueous 12% acetic acid | Fleischmann's Vinegar Company, Inc. 12604 Hiddencreek Way, Suite #A Cerritos, CA 90703 |
| grapeseed oil | Columbus Foods, 30 East Oakton St., Des Plaines, IL 60018 |
| Coal tar USP | Spectrum Chemical Manufacturing Corp., 769 Jersey Avenue, New Brunswick, NJ 08901-3605 |

Particularly for methods of treating basal cell carcinoma, coal tar topical solution can be substituted for coal tar USP. The U.S. Pharmacopeia provides the following description of how coal tar topical solution may be made in the USP Monograph for "Coal Tar Topical Solution".

TABLE 5 coal tar topical solution

| Ingredient | Concentration (v/v) |
|---|---|
| Coal tar | 200 g |
| Polysorbate 80 | 50 g |
| Alcohol, a sufficient quantity to make | 1000 ml |

Mix the coal tar with 500 g of washed sand and add the polysorbate 80 and 700 ml of alcohol. Macerate the mixture for 7 days in a closed vessel with frequent agitation. Filter, and rinse the vessel with sufficient alcohol to make the product measure 1000 ml. Preserve the product in tight containers. Alcohol content will be between 81% and 86%.

Yet another formulation, suitable for topical use in the treatment of basal cell carcinoma, is as follows:

TABLE 6 coal tar topical solution

| Ingredient | % of formulation (v/v) |
|---|---|
| Ethanol SDA 40B, 200 proof | 45.58 |
| Dipropylene glycol | 31.91 |
| Polyethylene glycol 600 | 13.67 |
| Coal tar USP | 1.55 |
| Grape seed oil | 7.29 |
| | 100% |

The ethanol, dipropylene glycol, and polyethylene glycol 600 are combined and mixed for 20 minutes. Coal tar is added to the mixture and blended for 60 minutes. Finally, the grape seed oil is added, and the formulation is mixed for another 60 minutes.

For a formulation suitable for injection, the ethanol SDA 40B, 200 proof is replaced by ethanol solution, denatured, sterile, made with USP water for injection, 70%.

Other formulations suitable for treatment of basal cell carcinoma include the following.

TABLE 7

| Ingredient | % of formulation (v/v) |
|---|---|
| Castor oil | 20-30% |
| Denatured alcohol | 20-30% |
| Coal tar USP | 0.05-2% |
| Xanthan gum | 1-3% |

TABLE 7-continued

| Ingredient | % of formulation (v/v) |
|---|---|
| Wintergreen oil | 0.025% |
| Deionized water | 40-55% |

TABLE 8

| Ingredient | % of formulation (v/v) |
|---|---|
| Aqueous 12% acetic acid | 20-35% |
| Grapeseed oil | 65-80% |
| Coal tar USP | 0.5-2.5% |

TABLE 9

| Ingredient | Amount |
|---|---|
| Coal tar | 50-250 g |
| Polysorbate 80 | 40-60 g |
| Alcohol, a sufficient quantity to make | 1000 ml. |

Table 10 discloses a solvent mixture that may be used to prepare a formulation of a coal tar product.

TABLE 10

| Ingredient | % of formulation (v/v) |
|---|---|
| DMSO | 50% |
| PEG 400 | 35% |
| Ethanol | 15% |

Example 4—Composition Derived from Coal Tar

This example discloses a composition derived from liquor carbonis detergens from Koppers, Inc. through fractional distillation and standard GCMS. It comprises a mixture of 17 fused, 3-ring arenes. The U.S. National Cancer Institute and other laboratories have shown that the individual molecules comprising this "cocktail" have minimal or no effect as oncolytics. In vitro assays have also shown that the composition does not inhibit the functioning of the pentose phosphate pathway in normal cells.

The composition is soluble in ethyl alcohol, DMSO, acetic acid, IPA, dichloromethane and dimethylformamide and is described in U.S. Pat. No. 6,337,337. See the table at column 4, lines 20-36, reproduced immediately below as Table 11 of this application.

TABLE 11

Composition constituents

| Hydrocarbon | Percent by weight |
|---|---|
| Phenanthrene | 21.1 |
| Fluoranthene | 9.07 |
| Anthracene | 7.45 |
| Biphenyl | 6.83 |
| Pyrene | 6.54 |
| Fluorene | 5.58 |
| Naphthalene | 4.08 |
| Carbazole | 3.41 |
| Dibenzofuran | 3.25 |
| 2-methylnaphthalene | 1.33 |
| Chrysene | 0.87 |

TABLE 11-continued

Composition constituents

| Hydrocarbon | Percent by weight |
| --- | --- |
| Benzo(a)anthracene | 0.76 |
| 1-methylnaphthalene | 0.63 |
| Acenaphthene | 0.46 |
| Indene | 0.40 |
| Quinoline | 0.30 |
| Tar Pitch | 27.93 |
| TOTAL | 100% |

One skilled in the art would understand that there is some variation possible in the concentrations of the individual components making up the composition. In particular, some of the lower concentration components may be dispensed with.

Optionally, compounds defined generically as tar pitch may be removed from the composition before it is used therapeutically. To remove the tar pitch and solid particulates not dissolved with solvents, a depth filter method may be used as, e.g., described at the Wikipedia website entry for "Depth filter".

Dark or brown discoloration of the basal cell carcinoma with the continuous application of a coal tar-based salve or solution can be a cosmetic issue for patients. One method of lightening the compound is to dilute it in any one of the solvents described herein and then filter this solution through activated charcoal.

As an alternative to the production of compositions from coal tar, compositions may be prepared by obtaining the individual chemical components listed above and mixing them in desired proportions. One such possibility is the composition produced by SPEXCertiPrep, CRM Division, Metuchen, N.J., the components of which are shown below in Table 12. This level of 1.27% final concentration of chemically-reproduced coal tar in a DMSO solution is sufficient to be used as a topical for BCC and can be diluted for use in the treatment of glioblastomas, if necessary. Compositions produced by mixing individual components will generally not include pitch. The adjustment of pH can be managed by the addition of sodium phosphate.

TABLE 12

Composition constituents

| Hydrocarbon mixture (1.27% of final solution) | Percent (wt/wt) |
| --- | --- |
| Phenanthrene | 29.3 |
| Fluoranthene | 12.6 |
| Anthracene | 10.3 |
| Biphenyl | 9.5 |
| Pyrene | 9.1 |
| Fluorene | 7.7 |
| Naphthalene | 5.7 |
| Carbazole | 4.7 |
| Dibenzofuran | 4.5 |
| 2-methylnaphthalene | 1.8 |
| Chrysene | 1.2 |
| Benzo(a)anthracene | 1.1 |
| 1-methylnaphthalene | 0.9 |
| Acenaphthene | 0.6 |
| Indene | 0.6 |
| Quinoline | 0.4 |
| | 100% |
| Hydrocarbon mixture (1.27% of final solution) | Percent by weight |
| Phenanthrene | 29.3 |
| Fluoranthene | 12.6 |
| Anthracene | 10.3 |
| Biphenyl | 9.5 |
| Pyrene | 9.1 |
| Fluorene | 7.7 |
| Naphthalene | 5.7 |
| Carbazole | 4.7 |
| Dibenzofuran | 4.5 |
| 2-methylnaphthalene | 1.8 |
| Chrysene | 1.2 |
| Benzo(a)anthracene | 1.1 |
| 1-methylnaphthalene | 0.9 |
| Acenaphthene | 0.6 |
| Indene | 0.6 |
| Quinoline | 0.4 |
| TOTAL | 100% |

1.27% (wt/wt) of the above hydrocarbon mixture may be mixed with 98.73% (wt/wt) DMSO solvent to obtain the final formulation. Different amounts of the hydrocarbon mixture and DMSO solvent may also be combined.

Mechanism of Action

The pentose phosphate pathway produces NADPH (nicotinamide adenine dinucleotide phosphate, reduced) at a high rate in all neoplastic cells for metabolism of tetrahydrofolate and rapid DNA synthesis, mitosis, and to produce enzymes to combat oxidative stress. The composition inhibits the hydrogen-donor functionality of NADPH during the conversion of dihydrofolate to tetrahydrofolate by means of either electron interference, non-competitive binding, or allosteric effect on NADPH. This arrests mitosis in neoplastic cells and thwarts gradual drug resistance by diminishing the cells' capacity to recycle glutathione and thioredoxin which scavenge excessive reactive oxygen species (ROS). The role of NADPH as an essential source of reducing power for neutralizing the high ROS levels of cancer cells can be found in Cairns & Harris, 2011, Cold Spring Harbor Symposia on Quantitative Biology 76:299-311.

Research Studies

The composition from Koppers, Inc. was tested at the U.S. National Cancer Institute in a one dose/60 cell line panel of cancer cell lines at a concentration of 100 µg/ml and was shown to be cytotoxic at a level of 100% to glioblastoma multiforme cells (U251) and by 91% to astrocytoma cells (SF-268). See FIG. 2.

The composition reduces the adherence of certain neoplasms to type IV collagen. Type IV collagen is responsible for the high density of cancer tumors. As an adjunct therapy, inhibition of cancer cell adhesion to type IV collagen would promote drug-penetration intratumorally by reducing the density of tumors and the "outward" systolic pressure they apply to flush out chemotherapeutics. In certain embodiments, the coal tar product can be combined with another chemotherapeutic or injected alone prior to the use of another drug to increase the tumor's porosity and reduce its ability to flush out the drug by systolic pressure.

TABLE 13

| Coal tar conc. μg/mL (% w/v) | % inhibition of adhesion of M14 cells to type IV collagen |
|---|---|
| 500 (0.5%) | 89% |
| 50 (0.005%) | 90 |
| 5 (0.0005%) | 62 |
| 0.5 (0.00005%) | 8 |

Glioblastoma is highly vascularized tumor with cells that are tightly compacted with high levels of collagen types IV and VI. It has been shown in human glioblastoma cell lines U251, U87MG and LN229 that type IV and type VI collagen promote upregulation of the angiogenic stimulant, vascular endothelial growth factor. Mammoto et al, *Role of collagen matrix in tumor angiogenesis and glioblastoma multiforme progression*, Am J Pathol. 2013 October; 183(4):1293-1305. Because Type IV collagen plays a supportive role in tumor angiogenesis and glioblastoma progression it is anticipated that a coal tar product, by inhibiting the binding of Type IV collagen to malignant cells within a glioblastoma tumor, would exhibit antiangiogenic effects and slow progression.

Liposomes, microspheres and drug-implanted polymers are feasible drug carriers for the composition.

2% and lower solutions of coal tar USP (from which the composition is sourced and purified) is considered safe by the FDA for transdermal delivery. See the creosote toxicology profile found at the Agency for Toxic Substances and Disease Registry's website.

Figure 8A:
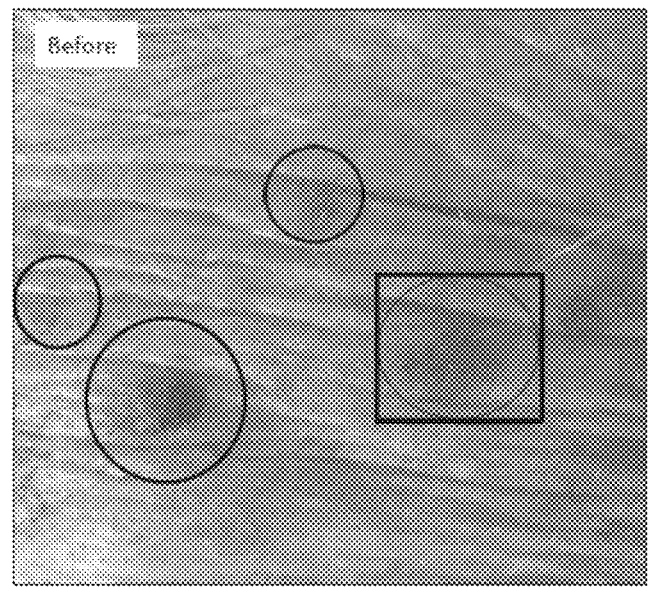
FIG. 8A-B shows close up views of the patient's left forehead before and after 12 days of 0.3% of the composition of Example 4 in alcohol solution applied topically twice daily. The images show loss of early stage BCC growths and BCC shrinkage. A, before application; B, after 12 days of application.
Figure 8B:
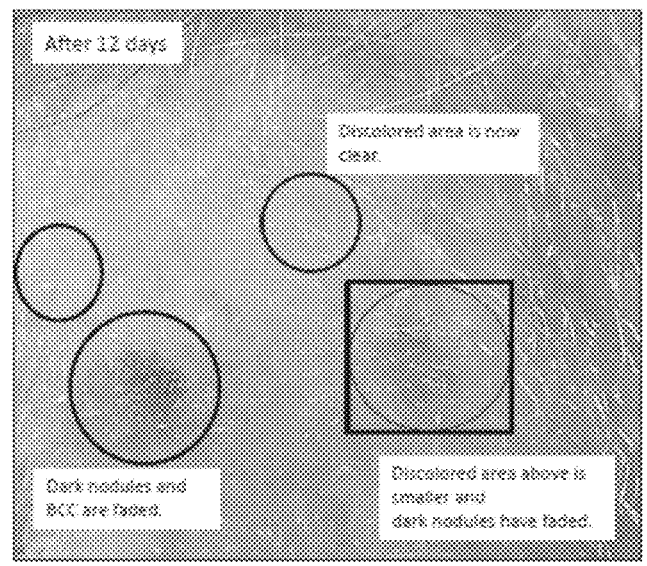

Example 5—Treatment Using Low Concentration of Composition Derived from Coal Tar Several early stage basal cell carcinomas on the patient's left forehead were treated for 12 days with 0.3% of the composition of Example 4 in DiPG/alcohol solution applied topically twice daily. This led to the shrinkage of the early stage basal cell carcinomas, as shown in FIG. 8A (before treatment) and FIG. 8B (after treatment).

What is claimed is:

1. A method for treating glioblastoma comprising administering to a patient in need thereof a therapeutically effective amount of a coal tar product.

2. The method of claim 1, wherein the coal tar product is present in a pharmaceutical composition.

3. The method of claim 2, wherein the pharmaceutical composition is administered using a technique selected from the group consisting of intravenously, subcutaneously, and by inhalation.

4. The method of claim 2, wherein the pharmaceutical composition is administered to a surgical cavity.

5. The method according to claim 4, wherein the pharmaceutical composition is administered to a surgical cavity utilizing a unit dosing dispensing device, a needle, a microneedle, a non-needle injection device, a prefilled applicator, a saturated wipe, or an adhesive bandage.

6. The method of claim 2, wherein the coal tar product is coal tar USP.

7. The method of claim 2, wherein the coal tar product is added to solvents or diluents and comprises the following:

| Hydrocarbon | Percent by weight |
|---|---|
| Phenanthrene | 29.3 |
| Fluoranthene | 12.6 |
| Anthracene | 10.3 |
| Biphenyl | 9.5 |
| Pyrene | 9.1 |
| Fluorene | 7.7 |
| Naphthalene | 5.7 |
| Carbazole | 4.7 |
| Dibenzofuran | 4.5 |
| 2-methylnaphthalene | 1.8 |
| Chrysene | 1.2 |
| Benzo(a)anthracene | 1.1 |
| 1-methylnaphthalene | 0.9 |
| Acenaphthene | 0.6 |
| Indene | 0.6 |
| Quinoline | 0.4 |
| TOTAL | 100%. |

8. The method of claim 2, wherein the pharmaceutical composition comprises:

| | |
|---|---|
| Coal tar USP | 0.005 to 2% |
| DiPG | 1% to 15% |
| Grapeseed oil or castor oil | 2% to 5% |
| Water | to 100% |

9. The method of claim 1 further comprising administering to the patient at least one additional treatment of the glioblastoma selected from the group consisting of temozolomide, carmustine, lomustine, vincristine, cisplatin, bevacizumab, etoposide, procarbazine; and a polylactic acid scaffold; or combinations thereof.

10. The method of claim 1, further comprising administering to the patient an alkylating agent.

11. The method of claim 1, further comprising administering to the patient an angiogenesis inhibitor.

12. The method of claim 1, wherein administering to a patient in need thereof a therapeutically effective amount of a coal tar product comprises topically applying to the lining of a post-surgical cavity a therapeutically effective amount of a coal tar product.

13. The method of claim 1, wherein a concentration of coal tar product is delivered to a tumor is sufficient to inhibit adhesion of cancer cells to type IV collagen.

14. The method of claim 13, wherein the adhesion of cancer cells to type IV collagen is inhibited by at least 8%.

15. The method of claim 1, wherein the coal tar product has a concentration between 0.5 μg/mL and 500 μg/mL.

16. A method of sensitizing glioblastoma to radiation treatment by inhibiting or interfering with the reducing-capacity of NADPH comprising administering to a patient having glioblastoma a therapeutically effective amount of a coal tar product.

17. The method of claim 16 wherein the patient is then administered a therapeutically effective dose of radiation at the same time as or after being administered the coal tar product.

* * * * *